US010352790B2

(12) United States Patent
Yanev et al.

(10) Patent No.: US 10,352,790 B2
(45) Date of Patent: Jul. 16, 2019

(54) FORCE MEASUREMENT DEVICE

(71) Applicant: ACTIVBODY, INC., Aliso Viejo, CA (US)

(72) Inventors: Kostadin Dimitrov Yanev, Monte-Carlo (MC); Stephen Vance Cooper, Amity, OR (US); Jonathan Victor Samuel Boro, Corvallis, OR (US); Ben Temple, Redmond, OR (US); Jesse Wayne Miller, Corvallis, OR (US); Ludmil Borissov Kalaydjiyski, Wiltshire (GB); Angel Georgiev Vassilev, La Jolla, CA (US)

(73) Assignee: ACTIVBODY, INC., Aliso Viejo, CA (US)

(*) Notice: Subject to any disclaimer, the term of this patent is extended or adjusted under 35 U.S.C. 154(b) by 0 days.

(21) Appl. No.: 15/861,913

(22) Filed: Jan. 4, 2018

(65) Prior Publication Data

US 2018/0188122 A1    Jul. 5, 2018

Related U.S. Application Data

(60) Provisional application No. 62/442,296, filed on Jan. 4, 2017, provisional application No. 62/478,467, filed on Mar. 29, 2017.

(51) Int. Cl.
*G01L 5/00* (2006.01)
*G01L 1/20* (2006.01)
*G01L 1/22* (2006.01)

(52) U.S. Cl.
CPC ............ *G01L 1/205* (2013.01); *G01L 1/2287* (2013.01); *G01L 5/00* (2013.01)

(58) Field of Classification Search
CPC .......... G01L 1/205; G01L 5/00; G01L 1/2287
See application file for complete search history.

(56) References Cited

U.S. PATENT DOCUMENTS

| 6,264,621 | B1 | 7/2001 | Paske |
| 6,358,187 | B1 | 3/2002 | Smith |
| 7,188,535 | B1* | 3/2007 | Spletzer ............... G01L 1/2206 |
| | | | 177/211 |
| 9,248,030 | B2* | 2/2016 | Amirouche ............ A61F 2/389 |
| 2005/0267485 | A1* | 12/2005 | Cordes ................... A61B 17/02 |
| | | | 606/88 |

(Continued)

FOREIGN PATENT DOCUMENTS

WO    2015/143281 A1    9/2015

OTHER PUBLICATIONS

Patent Cooperation Treaty, International Search Report for PCT/US2018/012363, dated Apr. 30, 2018, pp. 1-3.

*Primary Examiner* — Jamel E Williams
(74) *Attorney, Agent, or Firm* — Pillsbury Winthrop Shaw Pittman LLP

(57) ABSTRACT

Force measurement systems and methods are disclosed for accurate real-time measurement of forces. The system is configured to measure force as a function of time. The system may comprise a handheld device capable of measuring a force externally applied to opposing surface regions thereof for the purpose of monitoring or directing isometric exercises for personal wellness. Additionally, the system may be configured to communicate force measurement data to a remote device or server.

16 Claims, 11 Drawing Sheets

(56) References Cited

U.S. PATENT DOCUMENTS

| | | | |
|---|---|---|---|
| 2008/0306413 A1* | 12/2008 | Crottet | A61B 5/224 600/595 |
| 2009/0205875 A1 | 8/2009 | Claypool | |
| 2015/0362389 A1* | 12/2015 | Yanev | G01L 1/26 73/862.041 |
| 2016/0007909 A1 | 1/2016 | Singh et al. | |

* cited by examiner

FORCE MEASUREMENT DEVICE

CROSS-REFERENCE TO RELATED APPLICATIONS

This application claims priority to Provisional applications No. 62/442,296, filed on Jan. 4, 2017 and No. 62/478,467, filed on Mar. 29, 2017, which are expressly incorporated herein by reference in their entireties.

FIELD OF THE DISCLOSURE

The present invention relates generally to force measurement technology, and more particularly to a portable force measurement device for measuring force. The force measurement technology of the present invention can be incorporated into a number of different objects to interact with a user, which include, but are not limited to, hand-held devices or objects surrounding or in close proximity to a user that facilitate user interaction.

BACKGROUND

Apparatus used during personal or group exercise may be stationary or portable. Stationary apparatus may be configured to provide an exercise machine and quantify various aspects of an exercise routine, such as number of repetitions, calories burned, etc. Portable apparatus generally include much less functionality relative to larger, stationary apparatus and are often configured to monitor parameters such as heart rate, calories burned or strides taken while walking or running without providing an apparatus for exercise. Devices for measuring force and wirelessly communicating that force are known, for instance electronic bathroom scales configured to transmit a user's weight via a wireless communication protocol, however such devices are not configured to measure and transmit real-time force as a function of time, for instance while being squeezed between a the palms of a user's hands, nor are they designed for portable, handheld use during isometric exercise sessions. Portable exercise devices are useful when access to conventional exercise is inconvenient or unavailable. For example, air travel or other extended sedentary activities may restrict access to standard machines. The capability to track and record exercise provides additional benefit. For instance, users can set goals and performance targets. In medical monitoring applications, either a stationary apparatus or a portable device could be used to track performance and quickly screen for potential health concerns.

SUMMARY

The present disclosure describes systems and methods for measuring force.

The force measurement system described herein may, for example, be and/or be used in a portable device that facilitates isometric exercise by a user. In one or more embodiments, the system is configured to measure force and transmit the measured values to an external application in real time or near real time. However, this is not intended to be limiting. The present system may be used for other purposes and/or other functionality may be added to the device, depending upon the application. For example, the device may include an integrated 3-axis accelerometer, a gyroscope, and/or a geolocation (GPS) sensor. These additional features could provide information about the user's activity, motion and exercise intensity to complement the force measurement data.

The system may be used in connection with a variety of force-exerting activities developed around isometric training to exercise, rehabilitate, etc., muscles, muscle groups, and/or other body parts via isometric and/or other activities. The device may interact with application software, such as exercise tracking/coaching apps or games that enhance the exercise/rehabilitations experience. When interacting with applications, the applications may require the user to apply force to the device at varying intensities and for varying durations, for example.

The system may be and/or be incorporated into a number of different physical devices, for example a hand-held force measurement device. In such an embodiment, the system may be configured such that a user interacts with the force measurement system by engaging the exterior of the device by pressing different areas of the device together in a squeezing action (this is just one example and is not intended to be limiting). This application of force may cause a transfer of force to sensors (e.g., load cells and/or other sensors) inside a housing of the system. The system may be configured to include and process signals from other sensors such as temperature, heart rate, pulse oximetry, electrocardiography, etc. Individual sensors may comprise integrated strain gages configured to convert strain into a small change in resistance. With the application of a Wheatstone half-bridge, for example, and/or other arrangements of circuitry, the circuit outputs a measurable change in voltage, which can be converted into a force value. A second, closely coupled strain gauge may be used to compensate for temperature changes.

In some embodiments, the force measurement system comprises a housing body including a plurality of surface regions configured to receive forces exerted thereupon. At least two individual ones of the plurality of surface regions are configured to move relative to one another responsive to application of (e.g., isometric and/or other) forces on at least two individual ones of the plurality of surface regions. The one or more force sensors (e.g., load cells and/or other sensors) may be configured to generate output signals conveying information related to the forces. The force measurement system comprises a power supply and an electronics assembly including one or more processors and other electronic circuitry. In some embodiments, the electronics assembly is operatively coupled to the one or more force sensors and the power supply, for instance a battery. The force sensors, the power supply, and the electronics assembly are enclosed in the housing body. The one or more processors are configured by machine readable instructions (for instance software and/or firmware) to process the sensor output signals to convert and/or amplify the information related to the forces to produce a voltage signal. The force measurement system may be configured to determine individual or aggregated force values associated with the sensor output signals. In some embodiments, the force measurement system is configured to communicate the processed sensor output signals to a remote computing device not housed by the housing body. In some embodiments, the remote computing device is configured to receive and process multiple sensor output signals and determine individual or aggregated force values associated with the sensor output signals.

In some embodiments, the one or more force sensors comprise a plurality of load cells using strain gauges. The load cells may be spaced apart in peripheral regions of the housing body so as to provide a force sensing area. The force sensing area comprises an area where the aggregated force value is substantially the same regardless of a location in the force sensing area where the forces are received. The force sensing area may correspond to a shape and/or size of one or more of the plurality of surface regions. In some embodiments, the force measurement system comprises a plurality of load cells each affixed to cantilever beams, each having a fixed end and a free end; a frame assembly to which the load cells are fixedly attached, wherein the frame assembly is housed within, and floating with respect to, the housing body; and a plurality of activation members located such that at least one activation member is positioned between the free end of each cantilever beam and the housing body. In some embodiments, the one or more force sensors are selected from the group consisting of force sensing resistors, load cells using strain gauges, displacement sensors such as linear variable differential transformer (LVDT) devices, Hall Effect sensors and optical sensors, piezoresistive sensors, and pressure sensors.

In some embodiments, forces are exerted upon the housing by a user in the course of performing isometric exercise. A tare function may be implemented to account for a null offset value and/or drift in the strain gauge load cell signal in the absence of applied force. In some embodiments, the force measurement system further comprises a circuit configured to provide temperature compensation to enhance accuracy of the aggregated force value. In some embodiments, the value for the aggregated force applied to the housing body is determined to within an accuracy of +/−1 pound and/or within a linearity of +/−5 percent. In some embodiments, the force measurement system is further configured to convert, in real-time, analog signals conveying information related to repeated forces exerted upon the device into digital measurements, wherein the one or more processors are configured by machine readable instructions to provide real-time information to the user regarding the force applied to the housing body.

Another aspect of the present disclosure describes a force measurement method. The force measurement method is performed with the force measurement system. The method comprises receiving forces with the housing body, the housing body comprising the plurality of surface regions configured to receive the forces exerted thereupon. The plurality of surface regions may comprise shapes moveable relative to one another responsive to application of the forces on at least two individual ones of the plurality of surface regions. The method comprises generating, with the one or more force sensors, output signals conveying information related to the forces. The method comprises operatively coupling the power supply and the electronics assembly including the one or more processors to the one or more force sensors. The method comprises housing the one or more force sensors, the power supply, and the electronics assembly in the housing body. The method comprises executing machine readable instructions causing the one or more processors to: process the sensor output signals to convert and/or amplify the information related to the forces to produce a voltage signal; and communicate the voltage signal to the remote computing device not housed by the housing body. In some embodiments, the method further comprises determining, with the remote computing device, an aggregated force value associated with the sensor output signals.

DETAILED DESCRIPTION

Figure 1A:
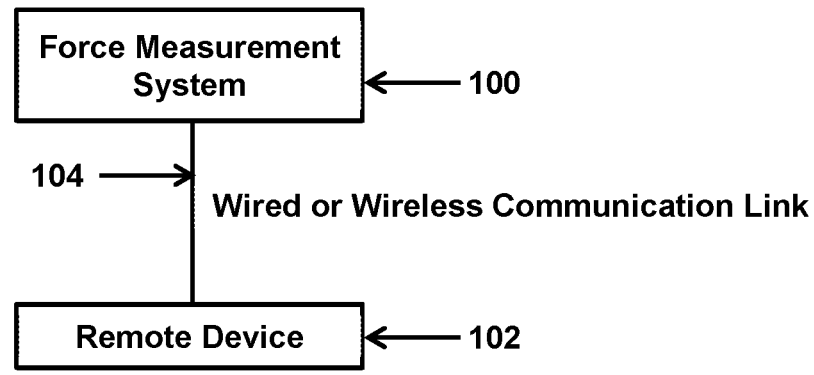
FIG. 1A is a schematic illustration of the force measurement system communicating with a remote computing device, according to one or more embodiments.

Embodiments of the present invention will now be described in detail with reference to the drawings and pictures, which are provided as illustrative examples so as to enable those skilled in the art to practice the invention. Notably, the figures and examples below are not meant to limit the scope of the present invention to a single embodiment, but other embodiments are possible by way of interchange of some or all of the described or illustrated elements. Wherever convenient, the same reference numbers will be used throughout the drawings to refer to same or like parts. Where certain elements of these embodiments can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the components referred to herein by way of illustration. Other and further aspects and features will be evident from reading the following detailed description of the embodiments, which are intended to illustrate, not limit, the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, the term "or" means "and/or" unless the context clearly dictates otherwise.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1A illustrates a force measurement system 100 configured to measure force and communicate with one or more remote devices 102 according to one or more embodiments of the invention. In a first embodiment, the force measurement system is configured to communicate processed sensor output signals to a remote computing device using a wired connection, or via a wireless communication link 104 using a wireless communication protocol. In an alternative embodiment, the force measurement system is configured to communicate the processed sensor output signals to a remote device via a cloud server 106 using a first wireless communication link 108 between the force measurement system and the cloud server, and a second wireless communication link 110 between the cloud server and the remote device. A person of ordinary skill in the art will readily recognize that the foregoing embodiments are not limiting, and that, for instance, wired connections may be substituted for any of the wireless links or vice versa without deviating from the scope of the invention.

The force measurement system 100 may operate in conjunction with a remote application running on a remote device 102 such as a personal mobile device or computer, mobile phone, tablet or other personal computing device. The force measurement device communicates with the application, which together may operate as a combined system. The force measurement device is capable of converting, in real-time, the repeated forces applied to the device into digital measurements and then communicates with the device in real-time to provide a user with information about the force the user is applying to the device. The system is configured to allow users to interact with various applications (e.g., fitness, gaming, physical therapy, biometrics, historical comparisons, calories expended, multi-user experiences and/or other applications) by applying force on an external shell of the force measurement system (described below).

Figure 1A:
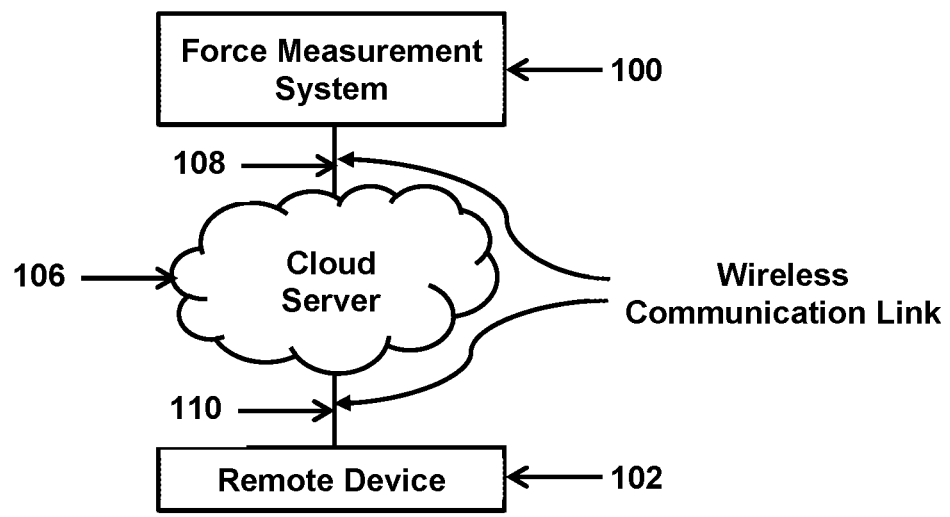
Figure 1B:
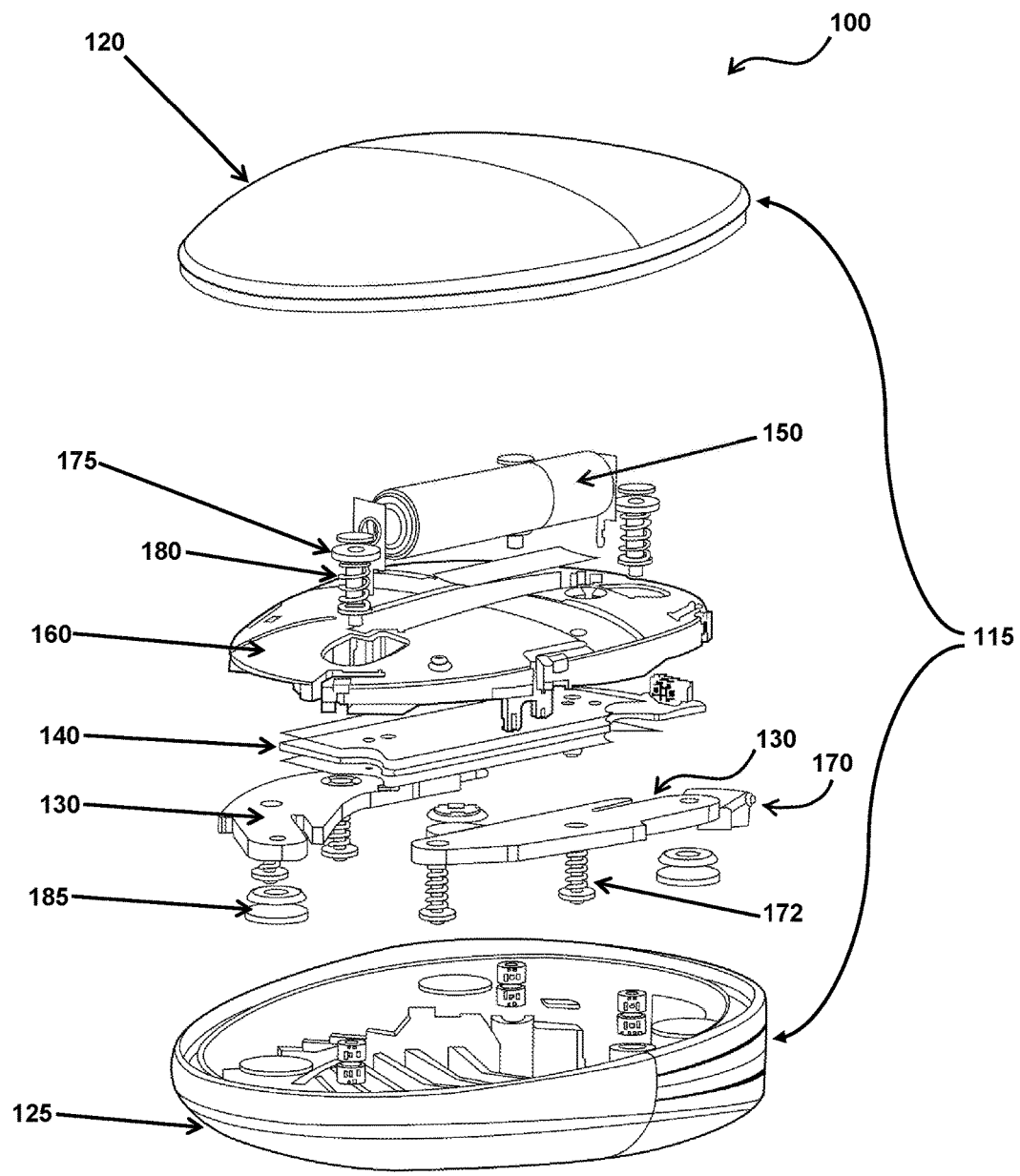
FIG. 1B is an assembly diagram depicting aspects of the force measurement system, according to one or more embodiments.

As illustrated in FIG. 1B and described in detail below, in operation, the system measures force and transmits the measured values to an external application in real time. The user interacts with the exterior of force measurement system 100 by pressing opposing surface regions of the system toward each other and/or in other directions. For example, this may be a squeezing action and/or other actions. A user may compress (e.g., squeeze) the surface of the system using any variation of body parts (e.g., using one hand, using two hands, using an elbow and a knee, using both knees, etc.), using a body part and a stationary surface (e.g., a wall, a desktop, etc.) and/or any other method. In some embodiments, the forces are caused by isometric exercises and/or other activities performed by a user. This application of force causes a transfer of force to pressure sensors inside the device, such as (e.g., high strength and/or other) load cells. In one or more embodiments described below, individual load cells comprise an integrated strain gauge to convert strain into a signal, for instance small change in resistance.

In some embodiments, the system circuitry employs a Wheatstone half-bridge strain gauge (though other force measurement technologies are contemplated) configured to enable the circuit to output a measurable change in voltage (based on the strain gauge's change in resistance under strain). A second, closely coupled virtually identical strain gauge is configured orthogonal to the measurement gauge to provide temperature compensation. In some embodiments, system firmware uses two-point linear calibration to convert voltages read from each load cell into force. Multiple force values are aggregated (e.g., summed and/or other aggregations) to determine the total force experienced by the device. By way of a non-limiting example, while in use, force measurements may be obtained every 100 ms and the results transmitted to a remote computing device. This transmission may be accomplished using, for example, Bluetooth® Low Energy (BLE), WiFi, LAN, USB, or any wired or wireless transmission method or protocol, including any standard, custom, or proprietary methods. The voltage from each strain gauge is amplified and then measured by an analog-digital converter (ADC), for example, of the electronics assembly 140 of the system (e.g., formed by and/or with one or more process including a printed circuit board comprising a microcontroller unit (MCU)) as described below.

FIG. 1B illustrates an embodiment of the force measurement system 100 of FIG. 1A. The system comprises a housing body 115 with a top case 120 and a bottom case 125 (the terms "top" and "bottom" are used for convenience only and are not intended to be limiting), and/or other components, configured to fit together and/or otherwise engage each other to form housing body 115. The housing body 115 may provide protection and/or mechanical support for components contained therein. The housing body 115 may form an outer shell of system 100, for example. The housing body 115 houses one or more force sensors 130, electronics assembly 140, a battery or other power source 150, a frame 160, and a light source (not shown) for providing information to the user via a light pipe 170. In some embodiments, the system 100 may further be equipped with an accelerometer and/or a gyroscope (not shown). In some embodiments, the housing body has a volumetric dimension of 115 cubic centimeters or less.

Force sensors 130 rely on and/or include one or more force sensing technologies. Applicable force sensing technologies may include, but are not limited to, force sensing resistors, load cells using strain gauges, displacement sensors (such as linear variable differential transformer (LVDT) devices, Hall Effect sensors and optical sensors), piezoresistive sensors and/or pressure sensors. Load cells may also be referred to as force sensors. The force sensors generate output signals conveying information used to determine force values for the force applied to the outer shell. The device further includes electronics assembly 140 comprising electronic circuits and firmware and/or other components configured to facilitate aggregation (e.g., summation) of the force values from the one or more force sensors to determine the total force applied on the outer shell (housing body 115) of system 100. In some embodiments, electronics assembly 140 may be configured such that the data collected by the sensors may optionally be collected and communicated to software residing remotely (e.g., on remote computing device 102 shown in FIGS. 1A and 1B) for calculating total force. In embodiments where the calculations are performed by the firmware on system 100, the total force applied may be communicated to remote application software.

As described in detail below, the outer surface regions of system 100 (e.g., surfaces of cases 120 and 125) are configured to enhance the user experience with system 100 by being smooth and free of sharp edges or pinch points, and provide protection for the internal components. These outer surfaces are constructed of materials, such as engineering plastics or elastomers, that have the ability to withstand the user applied force, to withstand the cyclical loading characteristic of isometric exercise, provide a water/sweat resistant barrier for the electronic components, withstand standard cleaning agents and chemicals, and are sufficiently sealed so that foreign ingress does not compromise the internal components. In some embodiments, an elastomer that is co-molded with plastic parts of sufficient hardness to provide for limited case motion, without introducing sharp-cornered gaps that can cause hazards.

Figure 2A:
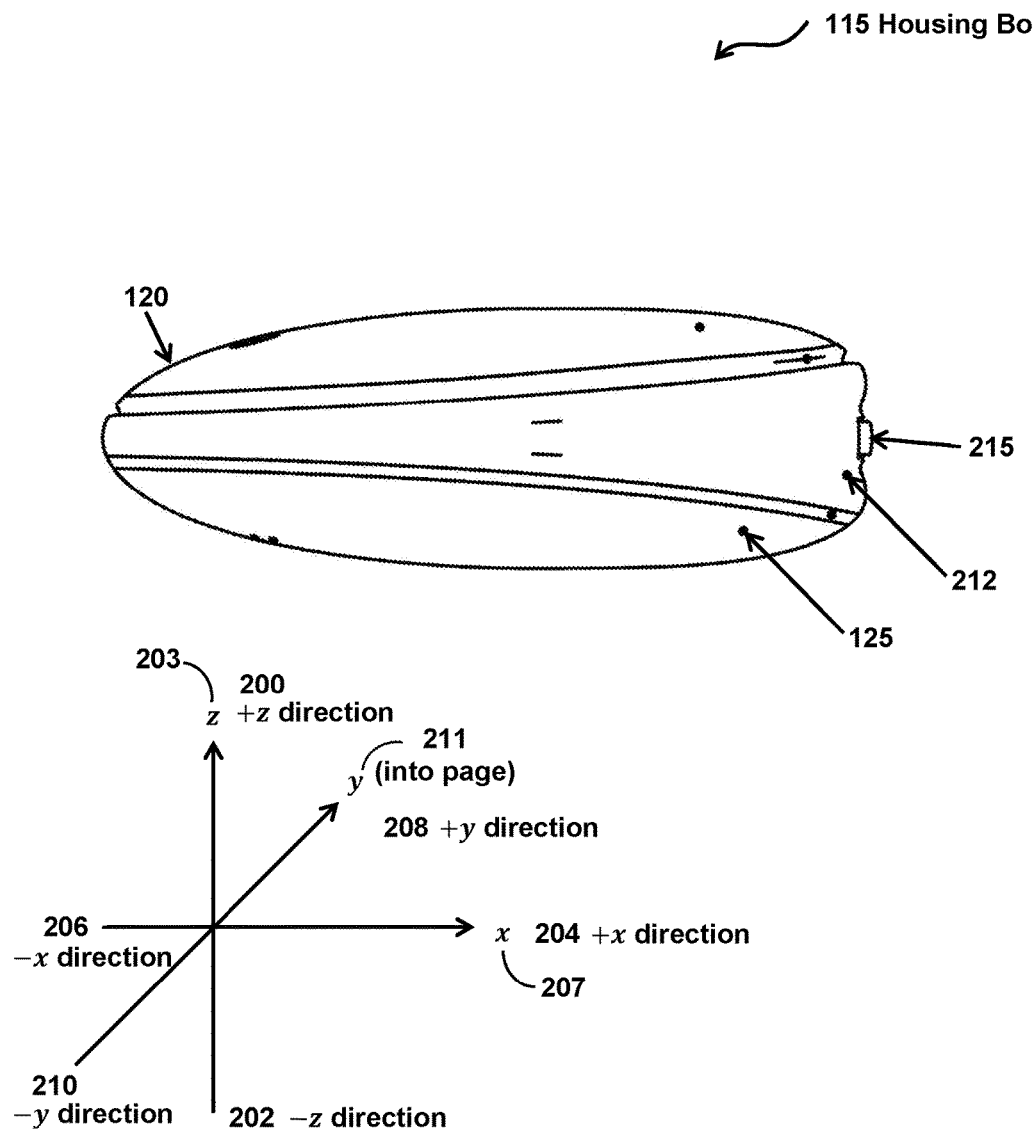
FIG. 2A illustrates a housing body and reference frame, according to one or more embodiments.

FIG. 2A illustrates a view of housing body 115 including cases 120 and 125. An orthogonal Cartesian coordinate system is defined as a frame of reference for this and subsequent figures. The positive z direction 200 is defined by a vector substantially normal to the center of the outer surface of top case 120 and pointing upward in FIG. 2A; the negative z direction 202 lies opposite, together forming the z axis 203. The positive x direction 204 is defined by a vector perpendicular to and intersecting the z axis, pointing to the right in FIG. 2A such that the x and z axes lie in the plane of the page of FIG. 2A; the negative x direction 206 lies opposite, together forming the x axis 207. The positive y direction 208 is defined by a vector orthogonal to the x and y axes and pointing into the plane of FIG. 2A; the negative y direction 210 lies opposite, together forming the y axis 211. As shown in FIG. 2A, the housing body 115 may incorporate a button or switch 215, an exterior portion of the light pipe 170 (FIG. 1B), and/or one or more light emitting diodes (LEDs; not shown) or other indicators, displays or user interface features.

The housing body 115 comprises at least a top case 120 and a bottom case 125 positioned opposite one another (e.g., along the z axis 203 in this example), wherein the two cases comprise shapes moveable relative to one another responsive to application of isometric (for example) and/or other forces on the outer surface regions of the cases, for instance in the +/−z directions 200, 202. In some embodiments, additional housing body components may comprise ergonomic shapes moveable relative to one another responsive to application of (e.g., isometric) forces on their outer surfaces. In some embodiments, the top and bottom cases may be attached to a belt 212 positioned therebetween, wherein the means for attachment allows for relative motion between the top and bottom cases, and/or to one or more other housing body components allowing for relative motion, for instance along the z axis, between the two cases. The ergonomic housing body is designed to optimize the comfort of the user and the accuracy of the force measurements.

Figure 2B:
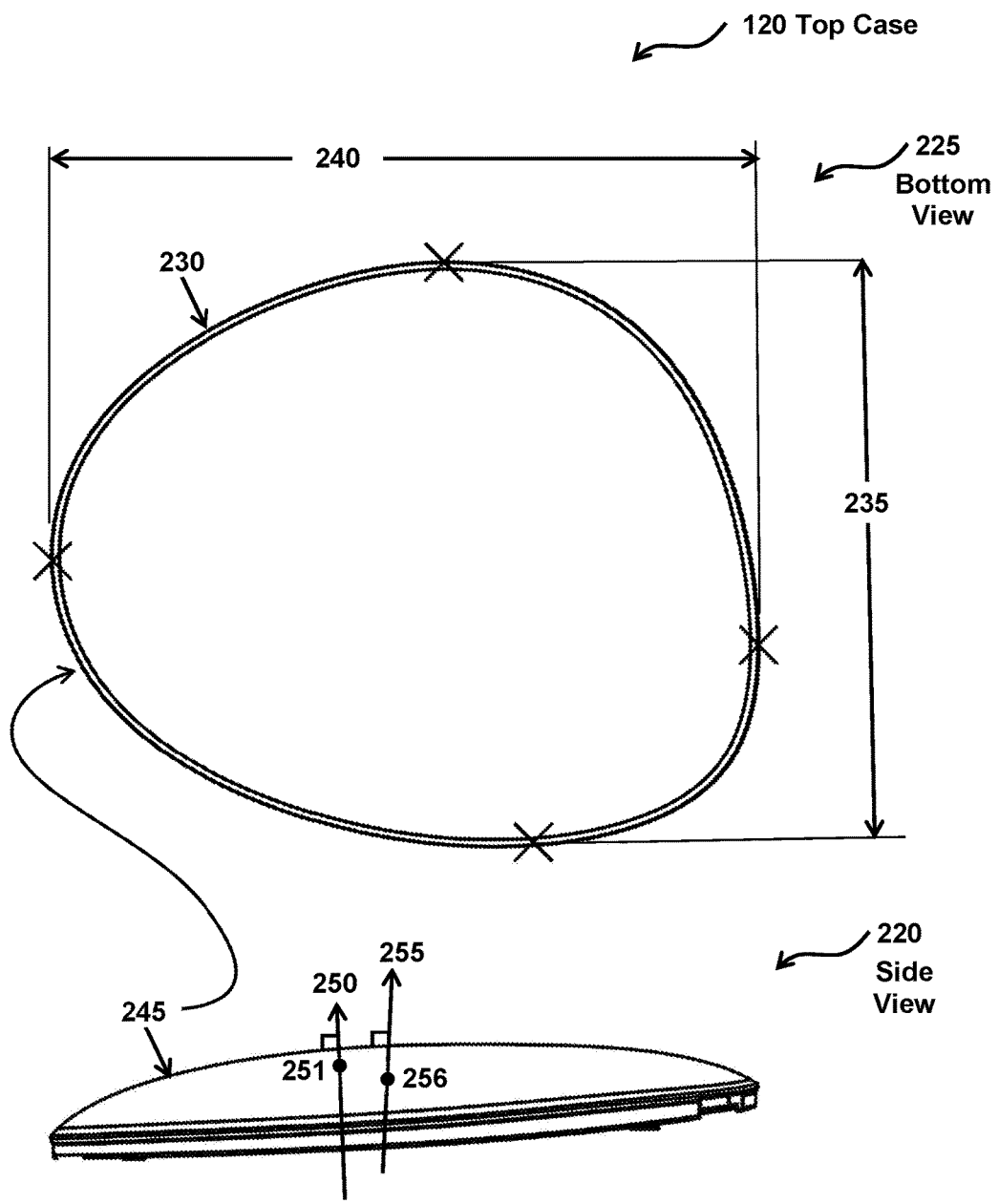
FIG. 2B illustrates an example of an embodiment of a first portion of the housing body, according to one or more embodiments.

FIG. 2B illustrates a side view 220 of the top case 120 of housing body 115 of FIG. 2A. The side view is from the same perspective as that of FIG. 2A, and the projected bottom view 225 with the x axis 207 and y axis 211 in the plane of the page and the positive z direction 200 into the page. A shape is defined at least in part by the perimeter 230 of the top case. In the depicted embodiment, the perimeter is neither round nor oval, but rather a smooth, continuous curve defining an ergonomic shape that is elongated along the x axis with respect to the maximum dimension along the y axis 235 that is less than the maximum dimension along the x axis 240. In some embodiments, the device geometry may be any shape designed to receive force from a user. For example, the top surface 245 may be straight, flat, curved, arcuate, dome shaped, and/or have one or more other shapes.

Referring to the side view 220 of the top case shown in FIG. 2B, the top case 120 of the housing body 115 has a convex and smoothly contoured outer top surface 245 designed such that a first vector 250 intersecting and normal to the surface at a first point 251 is generally not parallel to a second vector 255 intersecting and normal to the surface at a second point 256 for most or all pairs of points located on the outer surface of the top case.

Figure 2C:
FIG. 2C illustrates an example of an embodiment of a second portion of the housing body, according to one or more embodiments.

FIG. 2C illustrates a side view 260 of the bottom case 125 of housing body 115 of FIG. 2A. The side view is from the same perspective as that of FIG. 2A, and the projected bottom view 265 with the x axis 207 and y axis 211 in the plane of the page and the z direction 200 into the page. In this example, the shape defined by the perimeter 270 substantially mirrors that of the top case, and is elongated along the x axis with respect to the maximum dimension along the y axis 275 that is less than the maximum dimension along the x axis 280.

Referring to the side view 260 of the top case shown in FIG. 2C, the bottom case 125 of the housing body 115 has a convex and smoothly contoured outer bottom surface 285 designed such that a first vector 290 intersecting and normal to the surface at a first point 291 is generally not parallel to a second vector 295 intersecting and normal to the surface at a second point 296 for most or all pairs of points located on the outer surface of the top case.

In some embodiments, the top and bottom cases may be attached to a belt 212 positioned therebetween and providing an elastic connection between the top and bottom cases to form a housing (e.g., housing body 115) allowing for relative motion between the cases. In some embodiments, the belt may be incorporated into the top case 120 or the bottom case as shown in FIG. 2C. The system 100 may further include visual indicators to convey information to the user about the operation of the device, including, but not limited to, the state of the wireless connection, mechanical start and stop device activity and user control, which may be incorporated into any part of the housing body 115.

Figure 3A:
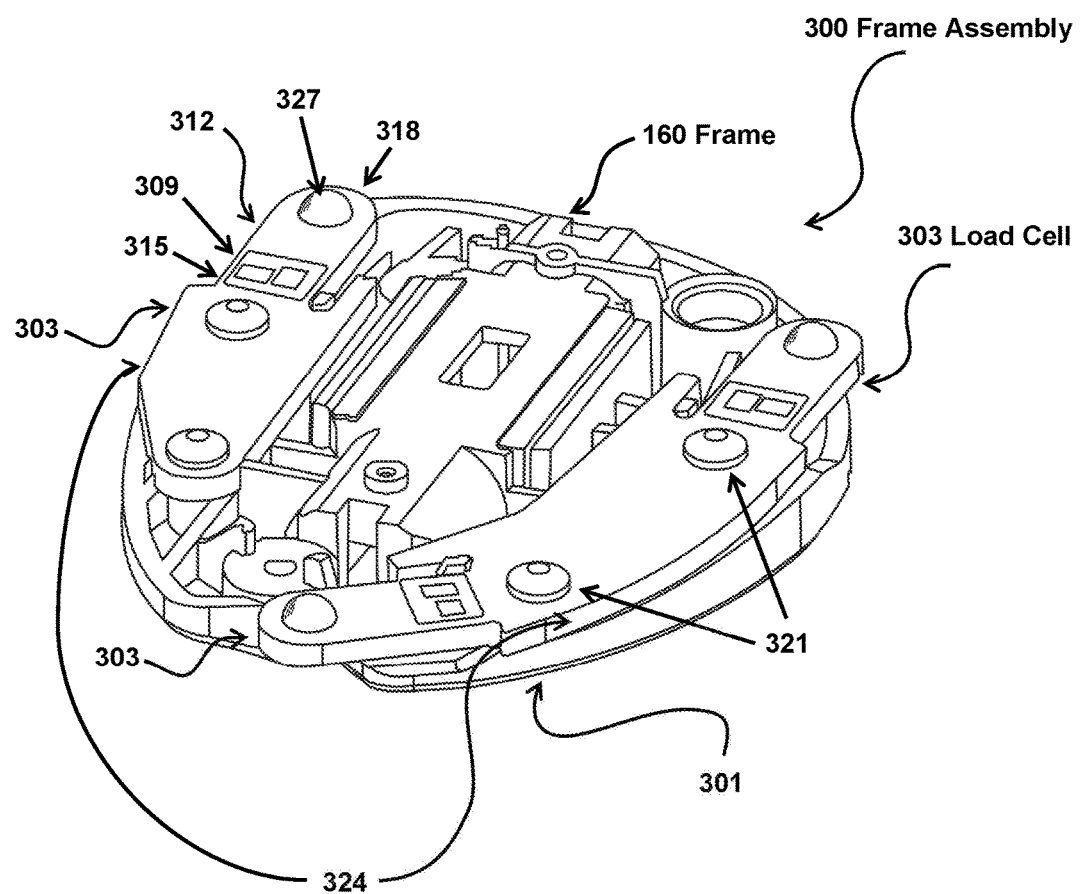
FIG. 3A illustrates an example of an embodiment of force sensors of the force measurement system, according to one or more embodiments.

FIG. 3A illustrates a frame assembly 300 comprising force sensors 130 (FIG. 1B) and/or other components configured to generate output signals conveying information related to forces and fixedly attached to a frame 160. In this example, the force sensors 130 comprise a plurality of load cells 303 each using a strain gauge 309, wherein the load cells are spaced apart in peripheral regions of the housing body so as to provide a force sensing area (also shown in FIGS. 2B and 2C) 301. The force sensing area 301 comprises an area where the aggregated force value (e.g., as described herein) is substantially the same regardless of a location in the force sensing area where the forces are received. As shown in FIGS. 2B, 2C, and 3A, the force sensing area corresponds to a shape defined by the load cell touch points projected upon the top and bottom surfaces where in the force applied may be accurately aggregated into a measurement by the system. The force sensing area may correspond in shape to one or more surface regions of housing body 115 of FIG. 2A. For instance the force sensing area may correspond to top surface region 245 bounded by top case perimeter 230 of FIG. 2B and/or bottom surface region 285 defined by perimeter 270 of FIG. 2C.

Individual load cells 303 comprise a cantilever beam 312, each having a fixed end 315 and a free end 318. As shown in FIG. 3A, the load cells are mounted on the frame 160, for instance using mechanical fasteners or anchors 172 positioned at anchor points 321. The strain gauges 309 and other components are fixedly attached to the cantilever beams, forming load cell subassemblies 324 that are attached to the frame 160 using mounting screws and/or by any other means of attachment. In some embodiments, a dimple 327 is located near the free end of the load cell, thereby providing a precise mechanical contact point from which to convey forces exerted on the outer surface regions of the force measurement system to the force sensor. The selected design approach provides the required force sensing accuracy at a lower cost, smaller size and larger active area than alternative designs. The value for the aggregated force applied to the housing body may be determined to within an accuracy of +/−1 pound and/or within a linearity of +/−5 percent. In order to better ensure accurate force measurement by the device, the force sensing frame assembly may be protected by creating over-travel geometries to limit the stress on sensitive structures.

Referring again to FIG. 1B, the frame 160 of FIG. 3A may be attached to the bottom case 125 of the device using mounting screws 175, such as shoulder screws mated to screw bosses in the lower case, and equipped with springs 180 to bias the frame to remain in contact with the load cells 303 while still allowing the frame assembly 300 to 'float' relative to the bottom case prior to adhesion. In some embodiments, the dimples 327 at the end of each of the three cantilever beams 312 contact the activation disks 185, which are supported by the bottom case. An adhesive and/or other coupling components may be used to join the cantilever beams and the activation disks in the area adjacent to each dimple. The adhesive holds the frame firmly to the bottom case, and allows for variations in manufacturing and assembly. The frame is allowed to 'float' along the z axis 203 relative to the bottom case, constrained in vertical translation by the bottom case mounting screws and accompanying springs, and is physically constrained along both horizontal axes 207, 211 by keying on one or more of the screw bosses. The top case 120 may, for instance, incorporate snap fit features to mate with interlocks on the frame to secure the top case to the frame.

Figure 3B:
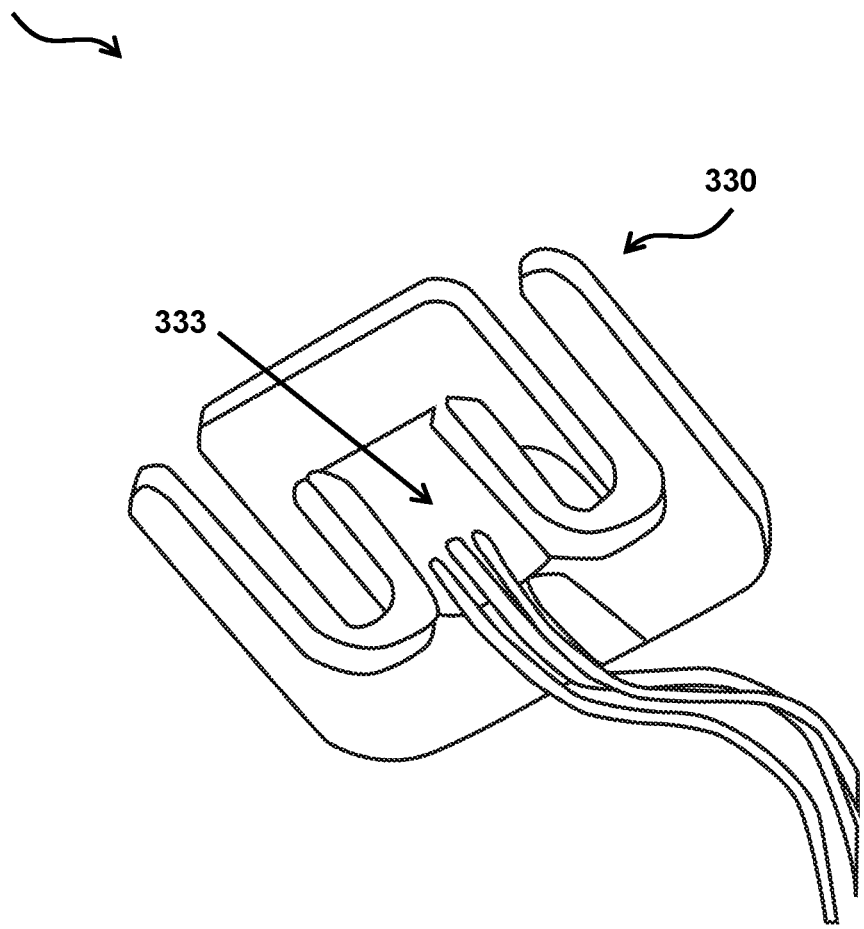
FIG. 3B illustrates an example of an embodiment of a load cell of the force measurement system, according to one or more embodiments.

FIG. 3B illustrates a portion of a force sensor 130 (FIG. 1) commonly available in the industry. In some embodiments, the design of the one or more force sensors may comprise a load cell 303 incorporating a strain gauge 309. Load cells can be created in a variety of possible geometries. Perhaps the most common is the "W" shaped load cell 330 for instance with a centrally located strain gauge 333 as shown in FIG. 3B. The sample embodiment of FIG. 3B is not intended to be limiting. For example, a variant is a "J" shape, which consists essentially of half of the W. Other possible geometries providing both positive and negative strain centered at the inflection point for increased accuracy (at a higher cost and larger size) include "U" and "S" shapes. The "I" geometry (a simple bending beam) is the most compact and lowest cost design, but it is less frequently used because the geometry provides a single polarity of strain and because of challenges in supporting the cantilever beam.

In the example illustrated in FIG. 3A, the load cells are configured as Wheatstone half-bridges with strain gauges 309 mounted on each of three cantilever beams 312. In some embodiments, the force measurement system 100 may comprise a cantilever load cell 303 (such as a simple "I" shaped cantilever load cell) with an attached strain gauge that changes resistance proportionally to deflection of the tip 318 of the cantilever beam as force is applied. The device may further include multiple anchor points 321 incorporated into the frame geometry and securing the cantilever to the frame 160 for more accurate measurements even at higher force levels and to realize a consistent inflection point. The multiple load cells may be spaced toward the periphery of the shell providing a large active area where force can be applied by the user with accurate force sensing (e.g., the force measurement area). The load cells may further be designed so that the load point 327 of the cell is as close as possible to the tip of the cantilever beam providing a large active (force measurement) area.

As the tip 318 of the cantilever beam 312 deflects due to a force exerted on outer surface regions such as top surface 120 and bottom surface 125 of the system, the Wheatstone half-bridge circuit outputs a measurable change in voltage. This voltage from each strain gauge is amplified and then measured by an analog to digital converter (ADC). The firmware loads two-point linear calibration and tare data from non-volatile memory and uses this data to convert voltages read from each load cell into force values. Three force values (one from each load cell) are aggregated or vector-summed to determine the total force experienced by the device. While in use, electronics assembly 140 (including one or more processors) may be configured such that force measurements are taken in a quasi-continuous manner, for instance every 100 ms, to yield real-time results that may be transmitted to a host device using, for example, BLE. This example is not intended to be limiting as any number of possible force signal collection algorithms (e.g., different frequencies, different communication techniques, etc.) would be recognized by one of ordinary skill in the art.

Half-bridge strain gauges may include at least one active piezoresistive element to sense elongation of the cantilever and at least one other identical active piezoresistive element acting as a reference for temperature compensation to ensure accurate force measurements across the temperature range. Thus some embodiments may further comprise a circuit configured to provide temperature compensation to enhance accuracy of the aggregated force value. Using one or more of these devices, force may then be calculated as a calibrated, scaled sum of multiple strain gauge readings. The device may be calibrated, for example, using a simple one-time calibration during manufacturing to ensure in the required accuracy. In some embodiments, the device may also be equipped with a force sensor recalibration capability.

For example, electronics assembly 140 (e.g., including one or more processors) may be configured such hat tare is used when weighing the contents of a vessel, where the vessel is first weighed empty, and then filled with the contents. The result of subtracting the empty weight from the full weight will yield the weight of the contents, while discarding the weight of the vessel. This concept of tare may be applied to the load measurement of one or more embodiments of the current invention. For instance, the "no load" weight may recorded as a null-offset value and stored in non-volatile memory while the device has been deliberately placed in a condition with no external force. Subsequent measurements are corrected by subtracting the recalled null-offset value from the reported force. The null-offset error is thus analogous to the "vessel" load to be discarded. A device may be 'calibrated' by means of a slope correction multiplier. This multiplier can be determined by applying a known weight to the device and recording the reported weight. By dividing the known weight by the reported weight, the software can store a slope correction multiplier, which can be used to quantify the measurements. Since this technique requires a known repeatable weight to be applied, this may be applied as part of an initial calibration, for example.

In some embodiments, electronics assembly 140 (e.g., the one or more processors) may be configured such that the application of linear correction techniques of null-offset correction and slope multiplier may be used for initial calibration or for subsequent calibration if the device encounters conditions that permanently effect the measurement.

FIB. 3C illustrates a frame 160 according to one or more embodiments of the invention, and is oriented such that the x axis 207 and y axis 211 of FIG. 2A lie substantially parallel to the plane of the page. Bottom view 350 is oriented such that the positive z direction 200 of FIG. 2A is oriented into the page, whereas top view 355 is oriented such that the z direction is pointing out of the page. In the illustrated embodiment, the shape of the perimeter 360 of the frame is substantially the same as that of the perimeter 230 of the top case and the perimeter 270 of the bottom case, but slightly smaller to allow the frame to fit within the housing body. In some embodiments, the frame may incorporate slots or grooves 365 to allow portions of the frame to flex in order to snap into the bottom case 125 or top case 120. In some embodiments, the slots may be L-shaped to optimize the snap's retention force.

The frame 160 includes through holes 370 for mounting screws 175 used to attach the frame to the bottom case and/or for other purposes. These holes may be configured to be 'slip fit' or slotted or clearance in order to facilitate proper datuming relative to the top and bottom cases housings. In some embodiments, slots may be designed to mate with protuberances on mating parts to fix or restrain the position of the mating part with respect to the frame. The frame also incorporates holes and/or wells for screw bosses 375 to anchor the frame to the bottom case at anchor points 321 of FIG. 3A. The frame may include a power source well 380 to hold a battery or other power source and/or features 385 to accommodate electrical connections to a power source. The frame may have support structures 390 to support the cantilever beams and provide additional bosses into which mounting screws may attach. The frame may further include means (not shown) for attaching an electronics assembly 140 of FIG. 1B such as one or more processors included on a printed circuit board (PCB).

Figure 3C:
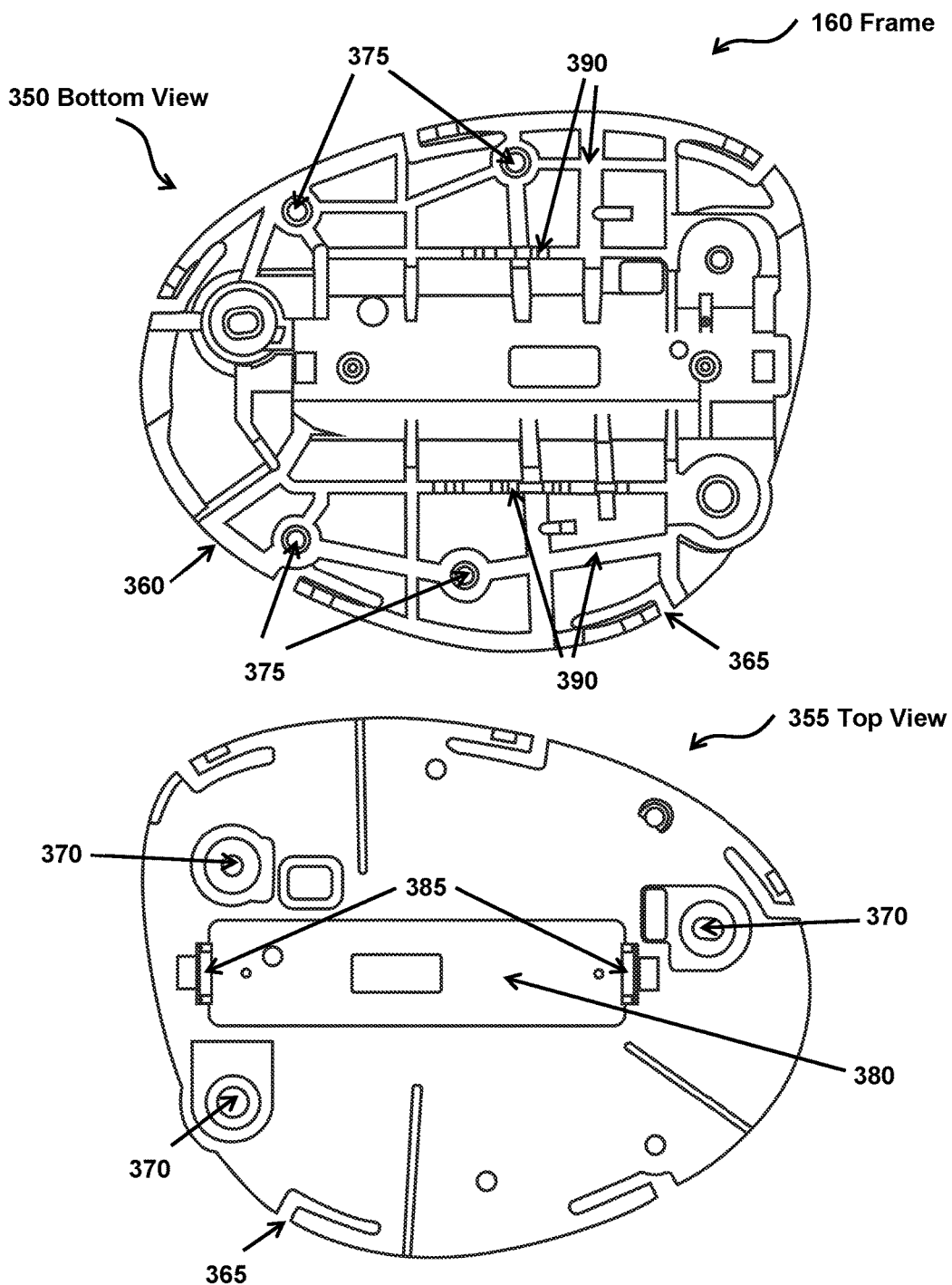
FIG. 3C depicts an example of an embodiment of a frame of the force measurement system, according to one or more embodiments.

Referring back to FIG. 1B, the force measurement system 100 may be powered by an electrical power source 150, such as a battery. The power source may be non-rechargeable or rechargeable. If the latter, the system 100 may be equipped with a charging port, e.g. a Universal Serial Bus (USB) charging port and/or other charging ports. If the former, the system 100 may be equipped with battery housing access for this purpose, for instance to a detachable battery housing. In the illustrated example, the power source is a single AAA battery, which lies in a slot 380 (FIG. 3) held in place by a pair of battery clips. The battery clips are fixedly attached to the frame 160 at each end of the battery slot and are fixedly connected to an electronics assembly 140 using, e.g., solder.

The electronics assembly 140 of FIG. 1B may comprise a printed circuit board (PCB) assembly containing one or more chipsets (e.g., one or more processors) configured to support wireless data transmission, such as BLE, and function as a microprocessor or MCU. A switch and one or more light emitting diodes (LEDs) and/or other type of light source may provide user feedback, and are also mounted on the PCB. The light source(s) may be multicolored, and may be optically connected to the outer case of the device by way of a molded light pipe. A switch, also mounted on the PCB, may be accessed through an elastomeric, molded-in button on the belt 212, for example. As further illustrated in FIGS. 1B and 3A, positioned below (e.g., in the orientation shown in the figures but this is not intended to be limiting) the PCB are the device's load cells 130, 303 and activation disks 185. The PCB assembly may be mounted to the frame 160 using screws or other means to secure it in place. There are electrical connections (not shown) between the PCB assembly and the strain gauges comprised by the load cells.

Figure 4:
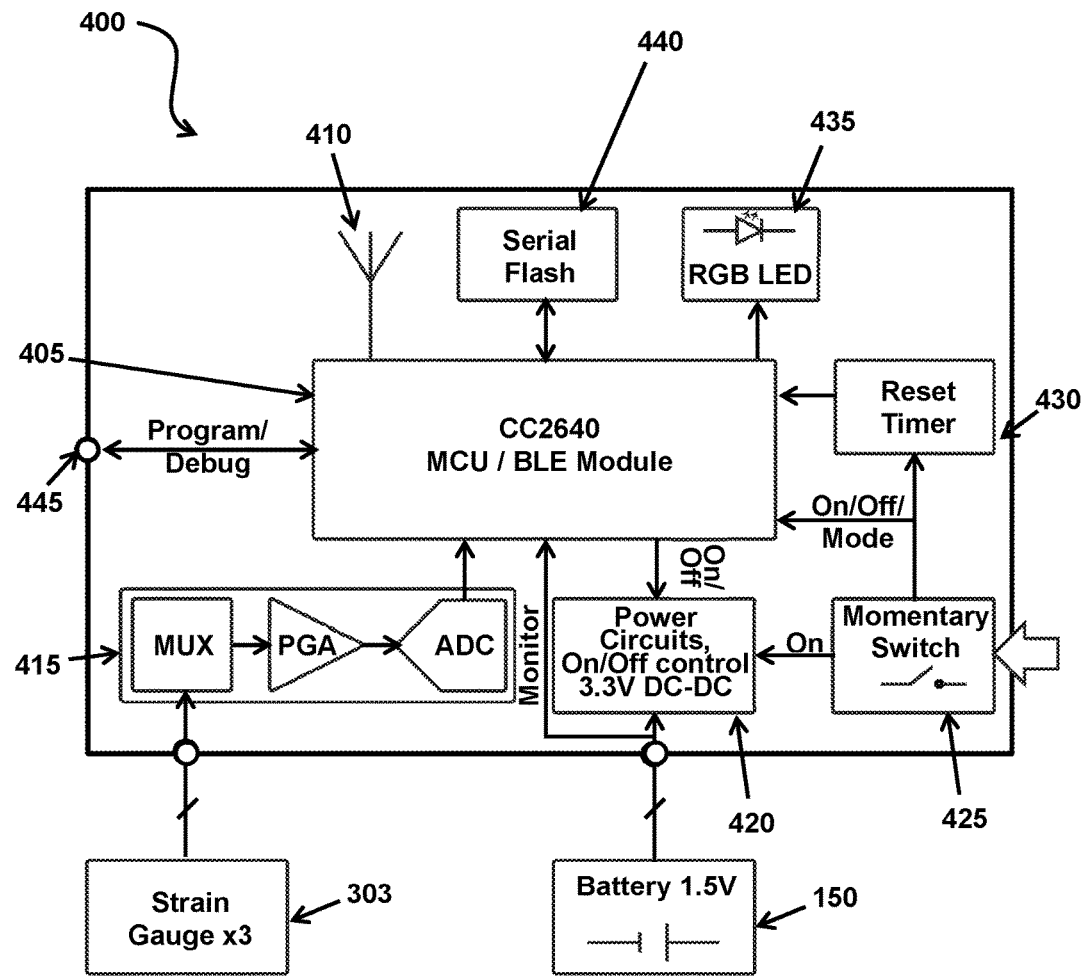
FIG. 4 is a block diagram illustrating electrical circuitry of the force measurement system, according to one or more embodiments.

FIG. 4 is a block diagram 400 illustrating the electrical circuitry according to one or more embodiments of the invention. The main electrical components and subsystems in the illustrated example include the following: an MCU/BLE chip module 405 configured to provide both processing capability and communication via BLE wireless communication protocol; a BLE antenna 410 configured to transmit and/or receive data; a MUX (multiplexer)/PGA (programmable gate array)/ADC module or modules 415 configured to provide a signal path for converting the strain gauge resistance into digital force measurements; power circuit module(s) 420 configured to convert battery voltage to voltage needed by circuitry and provide on/off control of device; a momentary switch 425 configured to provide on/off control; a reset timer 430 configured to decode button pushes; an RGB (red/green/blue) LED module 435 configured to provide red, green and blue indicator lights; a flash memory module 440 configured to persistently store the firmware image and other programmed data and provide capacity to store two images in case one is invalid or gets corrupted (e.g. by a failed firmware update); a program/debug port 445 such as a JTAG (Joint Test Action Group) port configured to provide access and/or capability for programming the device and outputting debug data. The electrical circuitry may be incorporated in whole or in part in the electronics assembly 140 and powered by a power supply 150 as shown in FIG. 1B. The power supply and force sensors 130 are electrically connected to the electrical circuitry. For example, the force sensors may be embodied as strain gauge load cells 303 as shown in FIG. 3A.

As noted, data transmission from the force measurement system 100 to the remote device 102 of FIG. 1A can be either wired or wireless, so as to enhance mobility, using BLE or other wireless transmission technology. If wireless transmission is used, the remote computing device may be equipped with an appropriate antenna. For example, an inverted F antenna may be included. The antenna geometry may be modified if required to accommodate the mechanical constraints of the device. The length may also require tuning to compensate for the size of ground plane on the PCB. The wireless technology may be either off-the-shelf or customizable so that the device can support use of a human interface device (HID) for compatibility with games designed for use with a mouse. For example, if BLE is employed to transmit data to the host device, BLE communication capability may be provided by a chipset with a reference design or a pre-certified module, such as the Texas Instruments (TI) CC2640 MCU/BLE chipset. Those skilled in the art will recognize that other chipsets and/or wireless communication protocols may be used without departing from the scope of the invention. The electrical circuitry may be mounted on a single PCB, thereby eliminating interconnections that may be unreliable, for example.

Firmware for the system 100 is configured to be run by the MCU 405 (the one or more processors), which controls the operations of the device, which may include, but not be limited to: turning power on and off in response to button pushes; connecting to the remote computing device by means of BLE or another wireless protocol; receiving and/or aggregating force information from the sensor output signals, analyzing and/or converting the output signals into a voltage signal, transmitting real-time force data to the remote device; signaling "exception conditions," such as low battery; and downloading and installing firmware upgrades using BLE or another wireless protocol. The firmware may operate as a single task under a real time operating system, for example. Events, including receipt of data, button pushes and expired timers, among other things, may be signaled by interrupts. The one or more processors (MCU 405) may also be configured with an automatic time-out function to preserve battery charge life.

Figure 5:
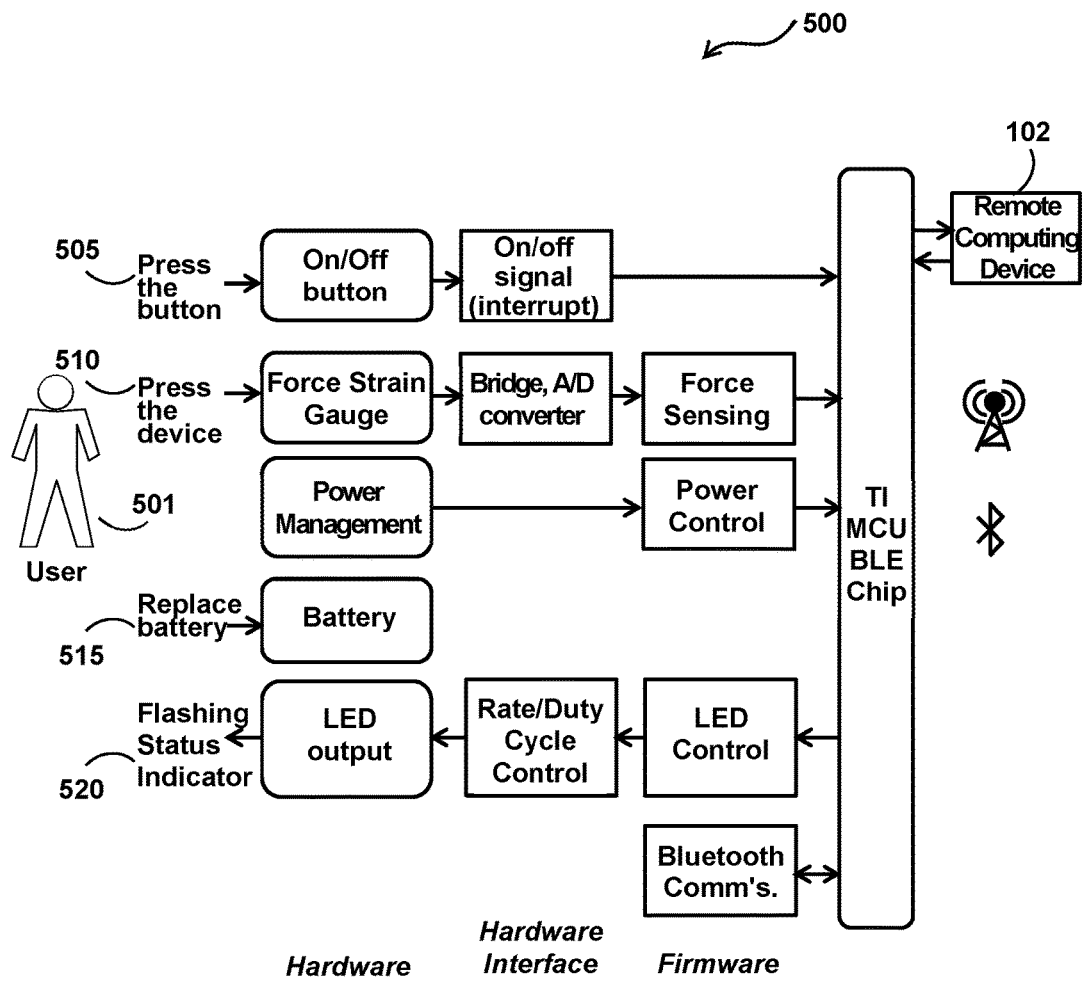
FIG. 5 is a diagram illustrating how a user interfaces with the force measurement system, according to one or more embodiments.

FIG. 5 is a diagram 500 illustrating how the user 501 interfaces with the force measurement system device 100 of FIG. 1. In the diagram, the boxes in the left column represent hardware, boxes in the middle columns represent hardware interfaces, and the boxes in the right column represent firmware functionality. As shown in FIG. 5, the user interacts with the device as described in the following steps, which need not be performed in the order shown. At step 505, the user uses a button (e.g. 215 of FIG. 2A) to turn the device on or off the device. At step 510, the user applies pressure to the outer surface regions (e.g., top case 120 and bottom case 125 of FIG. 1B) of the device to perform isometric exercises. At step 515, the user replaces or recharges the power source (e.g. 150 in FIG. 1B) when it is depleted. At step 520, the user observes the status of the device using the LED (e.g. 435 of FIG. 4).

Figure 6:
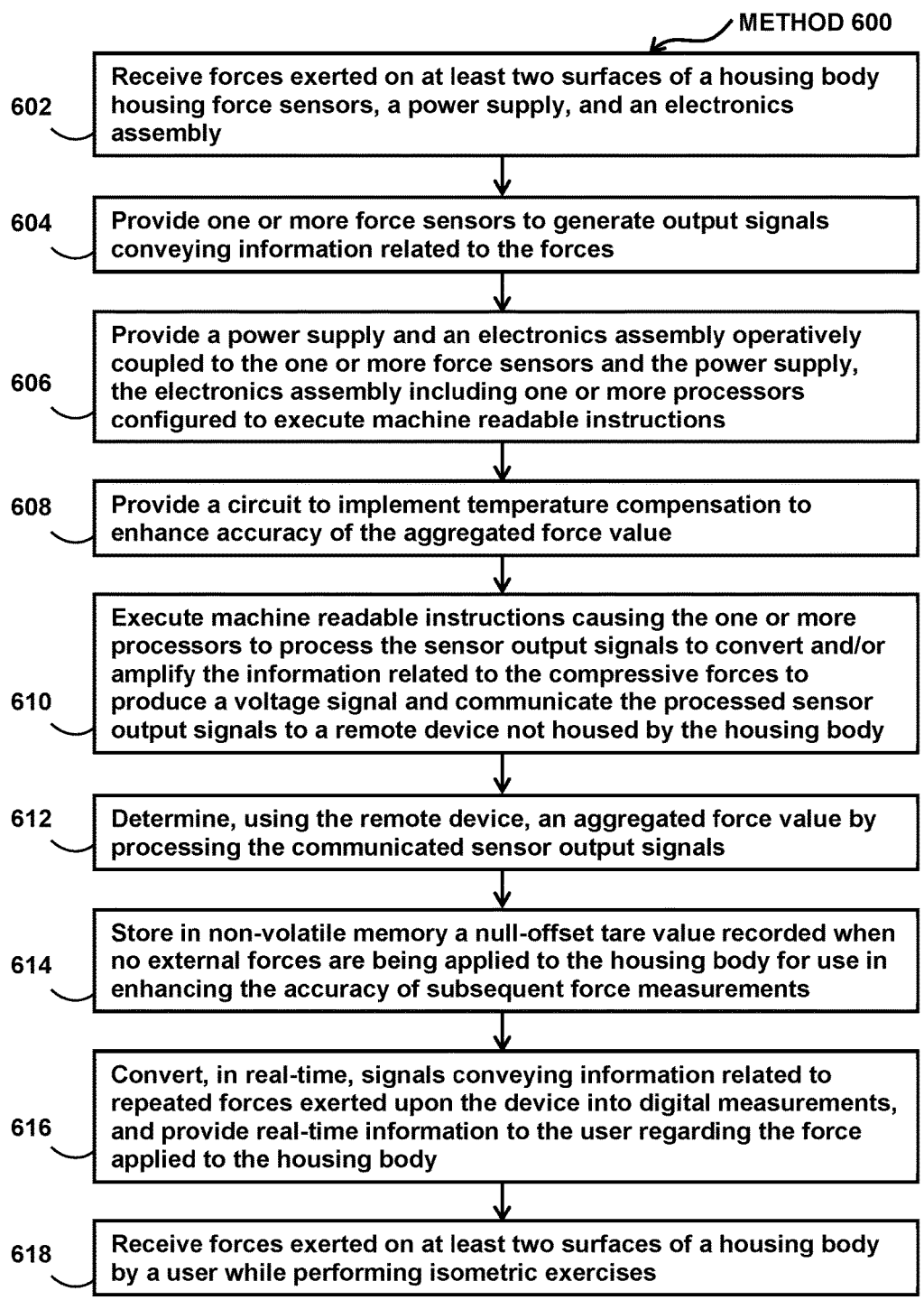
FIG. 6 illustrates a method for measuring force with a force measurement system according to one or more embodiments.

FIG. 6 illustrates a method 600 for measuring force with a force measurement system. The system comprises a housing body with a plurality of surface regions, one or more sensors, a power supply, an electronics assembly including one or more hardware processors configured to execute machine readable instructions, and/or other components. The machine readable instructions include instructions causing the one or more processors to convert and/or amplify the information related to the forces to produce a voltage signal, and instructions causing the one or more processors to communicate the processed sensor output signals to a remote device not housed by the housing body. The operations of method 600 presented below are intended to be illustrative. In some embodiments, method 600 may be accomplished with one or more additional operations not described, and/or without one or more of the operations discussed. Additionally, the order in which the operations of method 600 are illustrated in FIG. 6 and described below is not intended to be limiting. For example, in some applications it may be desirable to record and store the null-offset tare value and/or implement temperature compensation prior to determining any aggregated force values.

In some embodiments, method 600 may be implemented in whole or in part in one or more processing devices (e.g., a digital processor, an analog processor, a digital circuit designed to process information, an analog circuit designed to process information, a state machine, and/or other mechanisms for electronically processing information—MCU 405 including the one or more processors as described herein). The processing devices may include one or more devices executing some or all of the operations of method 600 in response to instructions stored electronically on an electronic storage medium. The processing devices may include one or more devices configured through hardware, firmware, and/or software to be specifically designed for execution of one or more of the operations of method 600.

At an operation 602, forces are received by a housing body housing force sensors, a power supply, and an electronics assembly. In some embodiments the forces are received by a housing body the same as or similar to housing body 115 (shown for example in FIG. 2 and described herein). In some applications, the forces may be isometric forces as described herein exerted on the housing by a user while performing isometric exercise and/or other forces and/or exercises.

At an operation 604, one or more force sensors are provided to generate output signals conveying information related to the forces. The one or more force sensors may be the same as or similar to sensors 130 (as shown in FIG. 1B and described herein) and may employ one or more force sensing technologies as described herein. In some embodiments, the signals are generated by using a Wheatstone half-bridge circuit in conjunction with strain gauge load cells the same as or similar to strain gauge load cell 303 (as shown FIGS. 3A and 3B and described herein).

At an operation 606, an electronics assembly the same as or similar to electronic assembly 140 (as shown in FIG. 1B and described herein) including one or more processors configured to execute machine readable instructions is provided. The electronics assembly is operatively coupled to the one or more force sensors described above and a power supply the same as or similar to power supply 150 (shown in FIG. 1B and described herein). In some embodiments, the electronics assembly may comprise a PCB as described herein. In some embodiments, the one or more processors may comprise an MCU/BLE chip module 405 configured to provide both processing capability and communication via BLE wireless communication protocol (as shown in FIG. 4 and described herein).

At an operation 608, a circuit is provided to implement temperature compensation to enhance accuracy of the aggregated force value. As described herein, half-bridge strain gauges may include at least one piezoresistive element to sense elongation of the cantilever and at least one other nominally identical piezoresistive element acting as a reference for temperature compensation to ensure accurate force measurements across the temperature range. Thus some embodiments may comprise a method using the reference piezoresistive element to provide temperature compensation to enhance accuracy of the aggregated force value.

At an operation 610, the one or more processors execute machine readable instructions causing the one or more processors to process the sensor output signals to convert and/or amplify the information related to the forces to produce a voltage signal. In some embodiments, the voltage signal may be produced using a Wheatstone half-bridge in conjunction with a strain gauge load cell as described herein. In addition, at an operation 610, the one or more processors execute machine readable instructions causing the one or more processors to communicate the processed sensor output signals to a remote computing device not housed by the housing body, the same as or similar to remote computing device 102 (as shown in FIG. 1A and described herein).

At an operation 612, a remote computing device the same as or similar to remote computing device 102 (as shown in FIG. 1A and described herein) determines an aggregated force value by processing the communicated sensor output signals. In some implementations, the aggregated force value may be determined by summing force values from a plurality of individual force sensors as described herein.

At an operation 614, a null-offset tare value recorded when no external forces are being applied to the housing body is stored in non-volatile memory the same as or similar to memory 440 (as shown in FIG. 4 and described herein). This value may be later recalled and used to enhance the accuracy of subsequent force measurements. In some embodiments, the null-offset tare value is subtracted from subsequent measurements as described herein. In some embodiments, a user enabled tare function could be built into the device to be summoned by the user to reset the null-offset tare value should components exhibit mechanical or electrical drift over time.

At an operation 616, signals conveying information related to repeated forces exerted upon the system are converted into digital measurements in real-time, and real-time information regarding the force applied to the housing body is provided to the user (e.g., via a remote computing device). For example force measurements may be obtained every 100 ms and the results transmitted to a remote computing device as described herein. This information may be transmitted using, for example, Bluetooth® Low Energy (BLE) using capabilities as or similar to those provided by 405 and 410 (as shown in FIG. 4) or transmitted by another connection as described herein.

At an operation 618, forces exerted by a user while performing isometric exercises are received by at least two surface regions of a housing body of a force measurement system 100 (as shown, for instance, in FIGS. 1A and 1B and described herein). The exercise-related forces may be measured as a function of time and/or transmitted to the user as described above. The system may transmit exercise information such as goals, instructions, parameters, or procedures related to performing an exercise. Exercise information may be preprogrammed and/or based on aspects of the user's performance as represented by data measured by or entered into the system.

In summary, the present invention provides a force measurement device having force sensors, including but not limited to load cells and strain gauges distributed about the periphery of the force measurement device for measuring the force applied to the exterior of the device. A force measurement device comprises an outer case acting as a housing body, an electronics assembly within the housing having hardware support for wireless communication, a power source and one or more force sensors distributed about the periphery of the device, where the outer case is capable of conveying force applied to the outer case to the one or more force sensors.

It will be understood, and is appreciated by persons skilled in the art, that one or more processes, sub-processes, or process steps described above and in connection with the figures may be performed by hardware and/or software. If the process is performed by software, the software may reside in software memory (not shown) in a suitable electronic processing component or system such as, one or more of the functional components or modules. The software in software memory may include an ordered listing of executable instructions for implementing logical functions (that is, "logic" that may be implemented either in digital form such as digital circuitry or source code or in analog form such as analog circuitry or an analog source such an analog electrical, sound or video signal), and may selectively be embodied in any computer-readable medium for use by or in connection with an instruction execution system, apparatus, or device, such as a computer-based system, processor-containing system, or other system that may selectively fetch the instructions from the instruction execution system, apparatus, or device and execute the instructions. In the context of this disclosure, a "computer-readable medium" is any means that may contain, store or communicate the program for use by or in connection with the instruction execution system, apparatus, or device. The computer readable medium may selectively be, for example, but is not limited to, an electronic, magnetic, optical, electromagnetic, infrared, or semiconductor system, apparatus or device. More specific examples, but nonetheless a non-exhaustive list, of computer-readable media would include the following: a portable computer diskette (magnetic), a RAM (electronic), a read-only memory "ROM" (electronic), an erasable programmable read-only memory (EPROM or Flash memory) (electronic) and a portable compact disc read-only memory "CDROM" (optical). Note that the computer-readable medium may even be paper or another suitable medium upon which the program is printed, as the program can be electronically captured, via for instance optical scanning of the paper or other medium, then compiled, interpreted or otherwise processed in a suitable manner if necessary, and then stored in a computer memory.

An electronic processing component or system such as, one or more of the functional components or modules, may be directly connected to one another or may be in signal communication. It will be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

Although the present invention has been described with reference to specific exemplary embodiments, it will be evident to one of ordinary skill in the art that various modifications and changes may be made to these embodiments without departing from the broader spirit and scope of the invention. Accordingly, the specification and drawings are to be regarded in an illustrative rather than a restrictive sense.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the present patent application has been described in detail for the purpose of illustration based on what is currently considered to be the most practical and preferred embodiments, it is to be understood that such detail is solely for that purpose and that the present patent application is not limited to the disclosed embodiments, but, on the contrary, is intended to cover modifications and equivalent arrangements that are within the spirit and scope of the appended claims. For example, it is to be understood that the present patent application contemplates that, to the extent possible, one or more features of any embodiment can be combined with one or more features of any other embodiment.

The invention claimed is:

1. A force measurement system, comprising:
   a housing body comprising a plurality of surface regions configured to receive forces exerted thereupon, wherein at least two individual ones of the plurality of surface regions are configured to move relative to one another responsive to application of the forces;
   one or more force sensors configured to generate output signals conveying information related to the forces;
   a power supply; and
   an electronics assembly including one or more processors, wherein the electronics assembly is operatively coupled to the one or more force sensors and the power supply, wherein the force sensors, the power supply, and the electronics assembly are housed by the housing body; and wherein the one or more processors are configured by machine readable instructions to:
      process the sensor output signals to convert and/or amplify the information related to the forces to produce a voltage signal; and
      communicate the voltage signal to a remote computing device, not housed by the housing body, and configured to receive the processed sensor output signals and determine an aggregated force value associated with the sensor output signals,
   wherein the one or more force sensors further comprise a plurality of load cells using strain gauges, wherein the load cells are spaced apart in peripheral regions of the housing body so as to provide a force sensing area corresponding to a shape and/or size of one or more of the plurality of surface regions and comprising an area where the aggregated force value is substantially the same regardless of a location in the force sensing area where the forces are received, and wherein the plurality of load cells comprise cantilever beams each having a fixed end and a free end, the system further comprising:
   a frame assembly to which the plurality of load cells are fixedly attached, wherein the frame assembly is housed within, and floating with respect to, the housing body; and
   a plurality of activation members located such that at least one activation member is positioned between the free end of each cantilever beam and the housing body.

2. The force measurement system of claim 1, wherein the one or more force sensors are selected from a group consisting of force sensing resistors, load cells using strain gauges, displacement sensors including linear variable differential transformer (LVDT) devices, Hall Effect sensors and optical sensors, piezoresistive sensors, and pressure sensors.

3. The force measurement system of claim 1, wherein the forces are isometric forces exerted upon the housing body by a user in the course of performing isometric exercise.

4. The force measurement system of claim 1, wherein the housing body has a volumetric dimension of 115 cubic centimeters or less.

5. The force measurement system of claim 1, wherein the housing body is configured to withstand a force of at least 200 pounds without sustaining substantial damage to the housing body or to the components housed therewithin.

6. The force measurement system of claim 1, further comprising a circuit configured to provide temperature compensation for the voltage signal to enhance accuracy of the aggregated force value.

7. The force measurement system of claim 1, wherein the plurality of surface regions, the one or more force sensors, and the electronics assembly are configured such that the value for the aggregated force applied to the housing body is determined to within an accuracy of +/−1 pound and/or within a linearity of +/−5 percent.

8. The force measurement system of claim 1, wherein the one or more processors are further configured by machine readable instructions to convert, in substantially real-time, output signals from the one or more sensors conveying information related to repeated forces exerted upon the at least two individual ones of the plurality of surface regions into digital measurements, and wherein the one or more processors are configured by machine readable instructions to provide substantially real-time information for display to a user related to the forces applied to the housing body.

9. A method for measuring force, comprising:
   receiving forces with a housing body comprising a plurality of surface regions configured to receive the forces exerted thereupon, wherein at least two individual ones of the plurality of surface regions are moveable relative to one another responsive to application of the forces;
   generating, with one or more force sensors, output signals conveying information related to the forces;
   operatively coupling a power supply and an electronics assembly including one or more processors to the one or more force sensors;
   housing the one or more force sensors, the power supply, and the electronics assembly in the housing body; and
   executing machine readable instructions causing the one or more processors to:
      process the sensor output signals to convert and/or amplify the information related to the forces to produce a voltage signal; and
      communicate the voltage signal to a remote computing device not housed by the housing body,
   wherein the method further comprises determining, with the remote computing device, an aggregated force value associated with the sensor output signals, wherein the one or more sensors comprise a plurality of load cells using strain gauges, wherein the load cells are spaced apart in peripheral regions of the housing body so as to provide a force sensing area corresponding to a shape and/or size of one or more of the at least two surface regions comprising an area where the aggregated force value is substantially the same regardless of a location in the force sensing area where the forces are received, the method further comprising:

provide the plurality of load cells with cantilever beams each having a fixed end and a free end;

fixedly attaching the plurality of load cells to a frame assembly, wherein the frame assembly is housed within, and floating with respect to, the housing body; and providing a plurality of activation members located such that at least one activation member is positioned between the free end of each cantilever beam and the housing body.

10. The force measurement method of claim 9, further comprising providing one or more force sensors selected from a group consisting of force sensing resistors, load cells using strain gauges, displacement sensors including linear variable differential transformer (LVDT) devices, Hall Effect sensors and optical sensors, piezoresistive sensors, and pressure sensors.

11. The force measurement method of claim 9, wherein the forces are isometric forces exerted upon the housing by a user in the course of performing isometric exercise.

12. The force measurement method of claim 9, wherein the housing body has a volumetric dimension of 115 cubic centimeters or less.

13. The force measurement method of claim 9, wherein the housing body is configured to withstand a force of at least 200 pounds without sustaining substantial damage to the housing body or to the components housed therewithin.

14. The force measurement method of claim 9, further comprising compensating the voltage signal, with a circuit housed by the housing body, for temperature variation to enhance accuracy of the aggregated force value.

15. The force measurement method of claim 9, further comprising determining the value for the aggregated force applied to the housing body to within an accuracy of +/−1 pound and/or within a linearity of +/−5 percent.

16. The force measurement method of claim 9, further comprising converting, in substantially real-time, output signals from the one or more sensors conveying information related to repeated forces exerted upon the at least two individual ones of the plurality of surface regions into digital measurements, and providing substantially real-time information for display to a user related to the forces applied to the housing body.

* * * * *